United States Patent [19]

Sakata et al.

[11] Patent Number: 5,318,906
[45] Date of Patent: Jun. 7, 1994

[54] AGENT FOR STIMULATING GROWTH OF ANIMAL CELLS AND SERUM-FREE MEDIUM CONTAINING SAME

[75] Inventors: Ko Sakata; Tetsuya Taekzono, both of Yokohama; Noritsugu Yabe; Hisao Matsui, both of Tochigi, all of Japan

[73] Assignee: Nippon Oil Company, Ltd., Tokyo, Japan

[21] Appl. No.: 893,647

[22] Filed: Jun. 4, 1992

[30] Foreign Application Priority Data

Jun. 5, 1991 [JP] Japan .................. 3-161043

[51] Int. Cl.⁵ .................. C12N 5/00; C12Q 1/00; C12P 1/00; A61K 35/78
[52] U.S. Cl. .................. 435/240.2; 435/7.21; 435/41; 424/195.1; 424/85.1; 424/85.2
[58] Field of Search .................. 424/195.1, 85.1, 85.2; 435/7.21, 41, 240.2

[56] References Cited

U.S. PATENT DOCUMENTS

| | | | |
|---|---|---|---|
| 4,317,816 | 3/1982 | Arichi et al. | 514/26 |
| 4,339,442 | 7/1982 | Takemoto et al. | 514/26 |
| 4,621,137 | 11/1986 | Miyake et al. | 536/5 |
| 4,684,628 | 8/1987 | Liu | 514/26 |
| 4,687,761 | 8/1987 | Liu | 514/26 |
| 4,849,355 | 7/1989 | Wong | 435/172.3 |
| 4,945,115 | 7/1990 | Liu | 514/731 |
| 4,956,355 | 9/1990 | Prendergast | 514/56 |
| 4,996,196 | 2/1991 | Mitsuhashi et al. | 514/5 |
| 5,071,839 | 12/1991 | Liu | 514/25 |

OTHER PUBLICATIONS

D. P. Stifes, et al "Basic & Clinical Immunology" 5th ed, Long & Med. Pub. Los Altos, Calif. pp. 86–92, 1984.
Hwang, et al., Korean J. Biochem. vol. 19, No. 2, 1987, pp. 89–102.
Sugaya et al., J. Ethnopharmacology, vol. 22, 1988, pp. 173–181.
Sarma et al., Annals of Botany vol: 65:37–40 (1990).
Chemical & Pharmaceutical Bulletin vol. 38, No. 12 Dec. 1990.

Primary Examiner—John W. Rollins
Attorney, Agent, or Firm—Testa, Hurwitz & Thibeault

[57] ABSTRACT

An agent for stimulating growth of animal cells in vitro comprises ginseng or an active ingredient extracted from ginseng Serum-free culture media containing the agent are disclosed. The present serum-free media contain less impure protein than serum-containing media, so that isolation and purification of substances produced by animal cells cultured therein is facilitated. The present serum-free media enhance the growth of lymphocytes in vitro, and can be used for vital cell transplant therapy, particularly for adoptive immunotherapy.

6 Claims, No Drawings

AGENT FOR STIMULATING GROWTH OF ANIMAL CELLS AND SERUM-FREE MEDIUM CONTAINING SAME

BACKGROUND OF THE INVENTION

The present invention relates to an agent for stimulating the growth of animal cells and a serum-free medium containing said agent. The agent is useful for stimulating the growth of animal cells, such as lymphocytes or hybridomas, which are difficult or unlikely to grow in a serum-free medium. The serum-free medium according to the present invention is employed as a medium for growing cells which produce physiologically active substances or for culturing cells for transplantation into a mammalian body.

Serum is the liquid portion that remains when blood clots spontaneously and the formed and clotting elements are removed, e.g., by centrifugation. Culture media for culturing animal cells typically contain about 5% to 20% serum in addition to amino acids, vitamins, sugars and inorganic salts. Animal cells stop growing and die in the absence of serum.

Serum is generally the most costly ingredient in culture media, accounting for about 75% to 95% of the cost. There are several drawbacks to the use of sera in culture media. For example, the quality of the sera can vary greatly between lots; sera are likely to be contaminated with Mycoplasma or viruses, and they cannot be sterilized with high-pressure steam due to the presence of serum proteins which would be denatured; and it is difficult to isolate and purify physiologically active substances produced by the animal cells cultured in serum-containing culture media due to the presence of the serum proteins. In order to overcome the disadvantages and drawbacks associated with serum-containing culture media, serum-free culture media have been employed.

A number of serum-free culture media are known, including, for example, a medium in which Eagle's MEM (Minimal Essential Medium) is used as a base medium to which albumin, insulin and/or transferrin are added; or a medium in which modified Eagle's MEM is used as a base medium, to which a factor for stimulating cells, which is obtainable by fractioning bovine serum with ammonium sulfate, is added. These serum-free media can be used in lieu of serum-containing media for culturing animal cells, however, they are less effective for growing these cells than serum-containing media. These media also are costly, and still contain residual serum elements even if fractioned. Serum-free media which are cost effective and which can be used to efficiently culture mammalian cells are needed.

SUMMARY OF THE INVENTION

The present invention provides an agent for stimulating the growth of mammalian cells in vitro comprising ginseng, or a product obtainable by treating ginseng, and serum-free media containing the agent. Serum-free media of the present invention contain little or no serum elements As a result of extensive studies and research on the effect of various ingredients for growing animal cells in serum-free media, it has been found that a type of ginseng, or a product obtained by extracting or otherwise treating ginseng, demonstrates a remarkable stimulatory effect on the growth of animal cells in vitro.

In one aspect, the present invention provides a serum-free medium for growing in vitro cells for use in vital cell therapies Vital cell therapies include, for example, adoptive immunotherapies, such as LAK therapy, TIL therapy and CTL therapy. In adoptive immunotherapy, lymphocytes are collected from the body of a cancer patient and activated or treated to enhance the cancer-killing properties of the lymphocytes. The present serum-free media are particularly useful for culturing lymphocytes for use in adoptive immunotherapy.

Serum-free media of the present invention stimulate the growth of mammalian cells in vitro to an equal or greater extent than serum-containing media without the drawbacks associated with serum-containing media. For example, use of the present serum-free media permits physiologically active substances produced by the cells to be more easily isolated and purified, resulting in a higher yield of the physiologically active substances than is obtainable from serum-containing media.

DETAILED DESCRIPTION OF THE INVENTION

Ginseng is a common name for plants of the genus Panax, a group of perennial herbs in the family Araliaceae. Ginseng traditionally has been thought to have prophylactic or therapeutic properties. Ginseng roots have been used medicinally in China for many years.

The present invention is based on the finding that ginseng or an extract or product obtainable by treating ginseng, can stimulate the growth of in vitro mammalian cells, such as lymphocytes, hybridomas and fibroblasts.

Ginseng species useful in the present invention include, for example, *Panax ginseng, Panax japonica, Panax quinquefolium, Panax notoginseng* and *Eluetherococcus senticosus*. The leaves, stem and root of the ginseng plant may be used, either raw or dried. Ginseng products obtained by treating the ginseng include processed products and cultured products. The processed products of the ginseng include products obtained by steaming or drying all or part of the ginseng plant. The cultured products include callus, liquid-cultured cells, differentiated organs, emerged roots (roots derived by infection with bacteria), and crown galls (obtainable by infection with bacteria) which are induced or cultured on the ginseng plant. Ginseng and biologically active products derived therefrom may be used as are (i.e., as they occur in the natural state), in a dry state, or in the form of an extract. Ginseng extracts are formed by contacting all or part of the ginseng plant with a solvent such as water, methanol or ethanol or a mixture thereof. The extract may further be treated or fractioned, for example, with activated carbon or a filtering gel, and may be used in a liquid form or as a dried powder obtained by spray drying or freeze drying (lyophilizing) the liquid extract.

The ginseng or the ginseng product may be used alone or in combination with a cytokine. The use of a cytokine in combination with ginseng or ginseng product extracted from ginseng is particularly effective for growing lymphocytes in vitro. Cytokines which can be used include, monokines and lymphokines. Monokines useful in the present invention include, for example, macrophage activating factors or monocyte activating factors. Lymphokines useful in the present invention, include, for example, interleukin-2, interleukin-3, interleukin-4, interleukin-6, B-cell growth factors, B-cell differentiation stimulating factors or $\gamma$-interferon.

Among the cytokines, interleukin-2 (IL-2) is particularly preferred for enhancing the cancer-killing activity of lymphocyte cells. The cytokine may be added to the medium in advance or concurrently with the ginseng and/or ginseng product Growth stimulating factors such as albumin, insulin or transferrin optionally may be added to the medium. The agents for stimulating the growth of the animal cells may be in the form of powder, granules or liquid.

The serum-free medium according to the present invention comprises a serum-free base medium and ginseng and/or ginseng product. The medium additionally may contain a cytokine and/or a growth stimulating factor, as described above. Any conventional serum-free culture medium or any modified culture medium in which animal cells can grow can be used as the base medium. Serum-free base media useful in the present invention include, for example, those commercially available under the trademarks ASF104 (Ajinomoto Co., Ltd.) and S-Clone SF-02 (Sanko Pure Chemical Industries, Ltd.). Serum-free media designated NOC-404, NOC-905 and NOC-909 (available from Nippon Oil Co., Ltd.) are particularly preferred. The major constituents of the base media NOC-404, NOC-905 and NOC-909 are set forth in Tables 1, 2 and 3 respectively.

TABLE 1

Major Components of Culture Medium NOC-404

| Components | Amounts (mg/liter) |
|---|---|
| Basal media | |
| Eagle MEM | 4,560[1] |
| RPMI-1640 | 5,040[1] |
| Amino acids | |
| L-Arginine HCl | 15 |
| L-Asparagine (H$_2$O) | 15 |
| L-Glutamine | 300 |
| Glycine | 5 |
| L-Proline | 5 |
| L-Serine | 30 |
| L-Threonine | 15 |
| L-Valine | 15 |
| Vitamins | |
| Cyanocobalamin | 0.01 |
| Biotin | 0.01 |
| Pantothenic acid-½Ca | 10 |
| Choline chloride | 25 |
| Other organic compounds | |
| d-Glucose | 500 |
| d-Mannose | 100 |
| Sodium pyruvate | 110 |
| Putrescine - 2HCl | 0.02 |
| Hypoxanthine | 0.1 |
| Thymidine | 0.025 |
| Ethanolamine | 20 |
| Hormones | |
| Human insulin | 10 |
| 3,3',5-Triiodo-L-thyronine-Na | 0.0065 |
| Metals | |
| Ferric chloride (6H$_2$O) | 5 |
| Copper sulfate (5H$_2$O) | 0.00002 |
| Zinc acetate (2H$_2$O) | 0.00002 |
| Selenous acid | 0.0014 |
| Chelating agents and buffers | |
| Dihydroxyethyl glycine | 815 |
| Glycyl glycine | 1,125 |
| Sodium hydrogen carbonate | 1,400 |

Note:
[1] a half of the ordinary concentration

TABLE 2

Major Components of Culture Medium NOC-905

| Components | Amounts (mg/liter) |
|---|---|
| Basal media | |
| Powder medium of mixture of RPMI-1640, Eagle MEM & Dulbecco's modified Eagle | 9,830 |
| Amino acids | |
| L-Alanine | 20 |
| L-Glutamine | 300 |
| L-Arginine HCl | 15 |
| L-Asparagine (H$_2$O) | 15 |
| Glycine | 5 |
| L-Proline | 5 |
| L-Serine | 15 |
| L-Threonine | 15 |
| L-Valine | 15 |
| Vitamins | |
| Sodium aspartate | 5 |
| Vitamin B$_{12}$ | 0.000125 |
| Biotin | 0.0025 |
| Other organic compounds | |
| Sodium pyruvate | 110 |
| d-Glucose | 100 |
| Choline chloride | 25 |
| Putrescine - 2HCl | 0.0125 |
| Hypoxanthine | 0.0025 |
| Thymidine | 0.00125 |
| Hormones | |
| Human apotransferrin | 10 |
| Human insulin | 10 |
| Metals | |
| Ferrous sulfate (7H$_2$O) | 1 |
| Sodium selenite | 0.0017 |
| Buffers | |
| Glycyl glycine | 1,500 |
| Sodium hydrogen carbonate | 1,400 |

TABLE 3

Major Components of Culture Medium NOC-909

| Components | Amounts (mg/liter) |
|---|---|
| Basal media | |
| Powder medium of mixture of RPMI-1640, Eagle MEM & Dulbecco's modified Eagle | 9,830 |
| Amino acids | |
| L-Alanine | 20 |
| L-Glutamine | 300 |
| L-Arginine HCl | 15 |
| L-Asparagine (H$_2$O) | 15 |
| Glycine | 5 |
| L-Proline | 5 |
| L-Serine | 15 |
| L-Threonine | 15 |
| L-Valine | 15 |
| Vitamins | |
| Sodium aspartate | 5 |
| Vitamin B$_{12}$ | 0.00125 |
| Biotin | 0.0025 |
| Other organic compounds | |
| Sodium pyruvate | 110 |
| d-Glucose | 100 |
| Choline chloride | 25 |
| Putrescine 2HCl | 0.0125 |
| Hypoxanthine | 0.025 |
| Thymidine | 0.0125 |
| Hormones | |
| Human apotransferrin | 10 |
| Human insulin | 10 |
| Human serum albumin | 2,000 |
| Metals | |
| Ferrous sulfate (7H$_2$O) | 1 |
| Sodium selenite | 0.0017 |
| Buffers | |

TABLE 3-continued

| Major Components of Culture Medium NOC-909 | |
|---|---|
| Components | Amounts (mg/liter) |
| Glycyl glycine | 1,500 |
| Sodium hydrogen carbonate | 1,400 |

The serum-free culture media according to the present invention may be a liquid or solid.

The concentration of the ginseng or ginseng product which is added to the culture medium can be in the range of from about 2 mg to about 10 mg per liter of serum-free medium. The amount is preferably from about 4 mg to about 6 mg, most preferably approximately 5 mg of dry ginseng extract per liter of medium.

The quantity of cytokine which can be added ranges from about 1 unit to about 2,000 units per ml of culture medium, and preferably from about 10 units to about 1,000 units per ml. The lymphokine can be used at substantially the same concentration. IL-2 preferably is added in an amount ranging from about 10 units to about 1,000 units per ml.

The serum-free medium according to the present invention optionally may contain a small amount of a serum-derived protein such as, for example, bovine serum albumin (BSA), but in an amount less than in conventional serum-containing media.

The agent and the serum-free medium containing the agent according to the present invention is useful for culturing animal cells in vitro, including lymphocytes, hybridomas and fibroblasts. Lymphocytes which can be cultured in the present media include, for example, cells derived from peripheral blood of a patient afflicted with acute lymphocytic leukemia or cells derived from lymphocytic tissues such as lymph nodes, pancreas, thymus, bone marrow or lymphoduct. The lymphocytes may include, for example, T-cells (e.g., helper T-cells, suppressor T-cells or killer T-cells) B-cells or NK-cells (Natural Killer cells). Hybridomas include hybridomas for producing antibodies and the like.

In a preferred embodiment, the agent and the serum-free media containing the agent according to the present invention are used to stimulate the growth of mammalian animal cells in vitro which are useful in vital cell transplant therapy. Vital cell transplant therapies include, for example, adoptive immunotherapy for cancer, autogenous bone marrow graft therapy, autogenous skin fibroblasts graft therapy, transplant of fetal Langerhans' islands primary cells to a patient with diabetes mellitus, transplant of fetal neurocytes to a patient with Parkinson's disease, and transplant of fetal liver cells to a patient with hemophilia. In each of these therapies, the cells of interest are removed from the body of a patient, cultured ex vivo, e.g., to activate them or increase their numbers, and then transplanted back into the patient For this purpose, culture media which can efficiently grow active animal cells is important.

In a preferred embodiment of the present invention, the present culture medium containing ginseng is used to culture lymphocytes for use in adoptive immunotherapy.

Adoptive immunotherapy generally involves collecting lymphocytes from the body of a patient with cancer, culturing the lymphocytes in vitro to enhance the ability of the cells to attack cancer cells, and introducing the lymphocytes back into the body of the cancer patient to preferentially kill the cancer cells. In some cases, cancer cells also are collected from the cancer patient and cultured together with the lymphocytes collected from the blood of the patient, thereby selectively proliferating killer T-cells, which in turn are transplanted back into the body of the patient. Killer T-cells are highly specific for the cancer cells.

These therapeutic techniques have fewer side effects than therapy with a carcinostatic agent, and are effective for metastatic cancers because the lymphatic cells which are transplanted are allowed to circulate in the body of the patient. Adoptive therapy may be generally classified into three kinds of therapy as follows:

1. LAK (Lymphokine Activated Killer) Cell Therapy

LAK therapy comprises collecting lymphocytes from the peripheral blood of a patient with cancer, culturing the lymphocytes together with IL-2 to activate the LAK cells, and transplanting the activated LAK cells back into the body of the patient. This method offers the advantage that the period for culturing the lymphocytes is relatively short, e.g., three to seven days. However, it suffers from several disadvantages: the resulting LAK cells are not very specific to cancer cells, they do not tend to accumulate at the site of the cancerous tissues, and this technique requires that IL-2 be administered in a large amount when the activated LAK cells are transplanted back into the body of the cancer patient.

2. TIL (Tumor Infiltrating Lymphocyte) Therapy

TIL therapy involves collecting lymphocytes from the site of a carcinoma in a cancer patient. Killer T-cell lymphocytes, which are highly specific for the cancer cells, are present in high concentrations at the site of the carcinoma. These lymphocytes are cultured with IL-2, thereby activating them. The activated cells are transplanted back into the body of the patient. This therapy is characterized in that the resulting TIL cells exhibit about 50 to 100 times the activity of the LAK cells used in LAK therapy, they have tumor specificity and the ability to accumulate in the cancerous tissues. TIL therapy, however, presents the problem that the period for culturing the lymphocytes is as extremely long, e.g., 30 to 60 days.

3. CTL (Cytotoxic T Lymphocyte) Therapy

CTL therapy involves collecting lymphocytes from the peripheral blood of a cancer patient, mixing the lymphocytes with cancer cells isolated from the site of a carcinoma in the patient, culturing the mixture of the lymphocytes and the cancer cells in vitro together with IL-2 to induce killer T-cells, and transplanting the induced killer T-cells back into the body of the patient. CTL therapy offers the advantage that the resulting killer T-cells are highly specific to the cancer cells and tend to accumulate in the cancerous tissues. CTL therapy is disadvantageous in that it is difficult to isolate the cancer cells from the site of the carcinoma and requires advanced administration into the patient of an inactivating agent (a carcinostatic agent) in order to inactive suppressor T-cells.

In order to further develop the vital cell transplant therapies described hereinabove, procedures for efficiently culturing lymphocytes and other mammalian cells in vitro are needed. Techniques for growing lymphocytes in particular in vitro must produce lymphocytes with high efficiency and safety for adoptive immunotherapy. The presence of serum in the culture medium used to grow these cells presents several problems, including contamination of the culture medium with mycoplasma and/or viruses, so that it is difficult to provide serum-containing culture media having a consistent quality. In addition, the cost of producing serum-containing culture media is high and it is difficult to separate the serum proteins from the cultured products of interest.

The use of serum-free culture media is preferred in order to avoid the problems associated with the use of serum. Growth factors can be included in the serum-free culture media if desired to further enhance growth of mammalian cells in the media. The present serum-free media containing ginseng, or a ginseng product resulting from treating or extracting ginseng, are favorable to growth of animal cells, while avoiding many of the disadvantages inherent in the use of conventional serum-free media and in serum-containing media. In these respects, the present invention is particularly useful for growing cells for use in vital cell transplant therapies.

The serum-free media of the present invention also are useful for culturing hybridomas. Monoclonal antibodies are of increasing importance to diagnosis and research, such as, for example, diagnosis of infectious diseases, purification of physiologically active substances by means of affinity chromatography, and target therapy. The present serum-free media containing ginseng and/or ginseng product are useful for stimulating the growth of antibody-producing hybridomas, including those producing polyclonal and monoclonal antibodies. Antibodies can be produced in high yields and at lower cost using the present media, and are more easily recovered due to the absence of serum in the media. The serum-free media according to the present invention are less subject to lot-to-lot variations in quality than serum-containing media. The serum-free media of the present invention permit antibodies to be isolated from the culture medium more easily due to the absence of serum proteins. Other physiologically active substances produced by animal cells cultured in the medium also are more easily separated from the medium because the present serum-free media do not require laborious procedures for purifying the substances.

The present invention will now be described more in detail by way of the following examples, which are not intended to be limiting in any way.

EXAMPLES

Example 1

To 25.07 grams of powder of *Panax ginseng* (Uchida Wakanyaku K. K.) was added 150 ml of a 40% ethanol aqueous solution, and the mixture was allowed to stand for one to three months for extraction. The resulting extract was filtered under vacuum through a Teflon ® filter (Mytex ®) having a pore size of 5 μm, thereby yielding a filtrate and a residue (roots). The filtrate was extracted with ethanol at 25°-34° C. by means of a rotary evaporator, yielding 82 ml of an extract which in turn was subjected to lyophilization to give 5.96 grams of powder of the extract from the ginseng.

Example 2

The extract powder was added to a serum-free medium for use in growing animal cells. To 1 liter each of NOC-905 medium (Nippon Oil Co. Ltd.) having the composition shown in Table 2, was added 2, 5 or 10 mg of the extract powder yielded in Example 1 to yield a series of liquid serum-free culture media having various concentrations of ginseng extract.

Example 3

A series serum-free culture media were prepared by adding and dissolving 2, 5 and 10 mg, respectively, of the extract powder obtained in Example 1 and 200 units of interleukin-2 (IL-2) 1 liter of NOC-905 medium to yield a series of liquid culture media having various concentrations of ginseng extract.

Example 4

The peripheral blood was collected from a human patient and a fraction of leukocytes was separated from the peripheral blood. To the fraction of leukocytes was added silica gel, latex or carbonyl ions for phagocytosing monocytes and macrophages so as to account for approximately 10% by weight of the mixture. This mixture was incubated at 37° C. for 1 hour, thereby removing the monocytes and macrophages, and the lymphocytes were collected in a conventional manner. The resulting lymphocytes were suspended in a serum-free medium (NOC-905) and the number of cells was counted.

The number of cells was adjusted to $10^6$ cells per ml, and the lymphocytes were inoculated into the serum-free media prepared in Example 3, containing various concentrations of the ginseng extract, and IL-2. A control medium containing neither IL-2 nor ginseng extract, and a second control medium containing just IL-2 were tested for comparison. The media containing the lymphocytes were incubated in a 96-well (6-10 rows) titre tray, each well having a capacity of 0.2 ml, in order to determine the relationship between the concentration of the ginseng extract and the growth of the lymphocytes. In the 4th day of incubation, $^3$H-thymidine was added to the media, and the media were further incubated for an additional 4 hours, allowing the lymphocytes to take up the thymidine.

The lymphocytes were adsorbed on a filter and washed with purified water, followed by immersing the filter in a cocktail solution and the strength of β-rays emitted from $^3$H-thymidine taken in by the lymphocytes was measured by means of a liquid scintillation counter. The ability of the human lymphocytes to take up $^3$H-thymidine is indicative of the level of DNA synthesis, which is directly related to cell growth. The results are shown in Table 4 (for first test) and Table 5 (for second test) below.

As shown in Tables 4 and 5, the growth of lymphocytes is directly related to the amount of ginseng extract in the medium. The maximum effect was produced under these conditions when the extract powder was present in an amount of 5 mg per liter. The growth-stimulating effect decreased when the extract powder was added in the amount of 10 mg per liter, as shown in Table 4.

The addition of IL-2 in an amount of 200 U/ml and the extract powder at the rate of 2-10 mg/liter to the base serum-free medium stimulates the growth of the lymphocytes by 1.7 to 2.6 times over that obtained when IL-2 alone was added in the same amount.

TABLE 4

| Base Medium | Amount of IL-2 (U-ml) | Amount of Extract Powder (mg/lit) | Radioactivity[1] DPM | Growth Multiplication |
|---|---|---|---|---|
| NOC-905 | 0 | 0 | 499.4 ± 74.0 | 0.32 |
| | 200 | 0 | 1567.5 ± 132.0 | 1 |
| | 200 | 5 | 4013.8 ± 331.5 | 2.56 |
| | 200 | 10 | 2612.2 + 189.3 | 1.67 |

Note:
[1] Value of radioactivity: average ± standard deviation

TABLE 5

| Base Medium | Amount of IL-2 (U-ml) | Amount of Extract Powder (mg/lit) | Radioactivity[1] DPM | Growth Multiplication |
|---|---|---|---|---|
| NOC-905 | 0 | 0 | 108.8 ± 16.8 | 0.04 |
| | 200 | 0 | 3088.0 ± 272.8 | 1 |
| | 200 | 2 | 6069.7 ± 226.2 | 1.97 |
| | 200 | 5 | 6635.1 + 685.1 | 2.15 |

Note:
[1] Value of radioactivity: average ± standard deviation

Equivalents

Those skilled in the art will be able to ascertain, using no more than routine experimentation, many equivalents to the specific embodiments described herein. Such equivalents are intended to be encompassed by the following claims

We claim:

1. A method for stimulating the growth of mammalian cells in vitro comprising culturing said mammalian cells in a serum-free medium comprising about 2 mg to about 10 mgll of medium of ginseng or a ginseng extract.

2. The method of claim 1, wherein the ginseng is selected from the group consisting of: *Panax ginseng, Panax japonica, Panax quinquefolium L., Panax notoginseng* and *Eleutherocuccus senticosus*.

3. The method of claim 1 wherein said ginseng extract is obtained by contacting the ginseng with water, alcohol or a mixture thereof.

4. The medium of claim 1 further comprising a cytokine.

5. The medium of claim 4 wherein the cytokine is a lymphokine.

6. The medium of claim 5 wherein said lymphokine is interleukin-2.

* * * * *

UNITED STATES PATENT AND TRADEMARK OFFICE
CERTIFICATE OF CORRECTION

PATENT NO. : 5,318,906
DATED : June 7, 1994
INVENTOR(S) : Ko Sakata, Tetsuya Takezono, Noritsugu Yabe
and Hisao Matsui It is certified that error appears in the above-indentified patent and that said Letters Patent is hereby corrected as shown below:

On the title page: Item [75] the second inventor should read

Ko Sakata; Tetsuya Takezono

Signed and Sealed this

Sixth Day of September, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,318,906
DATED : June 7, 1994
INVENTOR(S) : Ko Sakata, Tetsuya Takezono, Noritsugu Yabe and Hisao Matsui It is certified that error appears in the above-indentified patent and that said Letters Patent is hereby corrected as shown below:

Column 10, Line 12, in Claim 1, "10 mgl1" should be ---10 mg/L---.

Signed and Sealed this

Tenth Day of January, 1995

Attest:

BRUCE LEHMAN

Attesting Officer

Commissioner of Patents and Trademarks